US006951548B1

(12) United States Patent
Einstein

(10) Patent No.: US 6,951,548 B1
(45) Date of Patent: Oct. 4, 2005

(54) BLOOD IRRADIATING APPARATUS

(75) Inventor: George Einstein, Palm Beach, FL (US)

(73) Assignee: Einstein Clinical Laboratories S.A., Palm Beach, FL (US)

( * ) Notice: Subject to any disclaimer, the term of this patent is extended or adjusted under 35 U.S.C. 154(b) by 319 days.

(21) Appl. No.: 10/124,517

(22) Filed: Apr. 17, 2002

(51) Int. Cl.[7] .................... A61M 37/00; A61M 1/36; A61L 9/00; C02F 1/44
(52) U.S. Cl. .................. 604/6.08; 604/20; 604/27; 422/44; 422/24; 210/645
(58) Field of Search .............. 604/4.01, 5.01, 604/6.01, 6.09, 5.04, 6.08, 20, 27; 600/9; 210/205, 645; 422/44, 24, 28

(56) References Cited

U.S. PATENT DOCUMENTS 2,308,516 A    1/1943  Knott
4,578,056 A *  3/1986  King et al. ............... 604/6.08
5,433,738 A    7/1995  Stinson
6,113,566 A    9/2000  Schleicher
6,312,593 B1  11/2001  Petrie

* cited by examiner

*Primary Examiner*—Angela D Sykes
*Assistant Examiner*—Leslie R. Deak
(74) *Attorney, Agent, or Firm*—Gold & Rizvi, P.A.; H. John Rizvi; Glenn E. Gold

(57) ABSTRACT

A blood irradiating apparatus is provided including a plurality of irradiating chambers having a base and an openable cover. Each irradiating chamber will include a number of ultraviolet light bulbs configured to provide a wide spectrum of ultraviolet light of differing wavelengths. A number of cuvettes permeable to ultraviolet light will be disposed in the irradiating chamber and configured to permit blood to flow in a turbulent manner sufficient to maximize exposure to ultraviolet light. An adaptable tubing structure will be provided to strategically transport blood through a number of cuvettes for exposure to ultraviolet light during treatment.

14 Claims, 9 Drawing Sheets

FIG. 3
FIG. 4
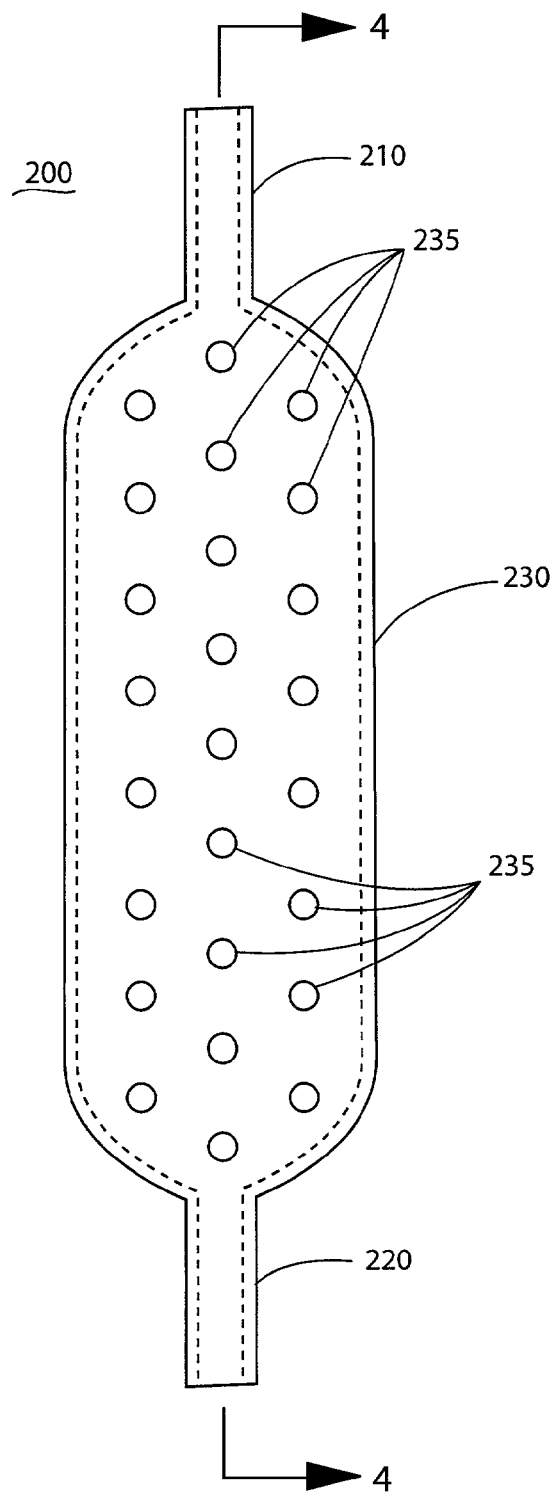
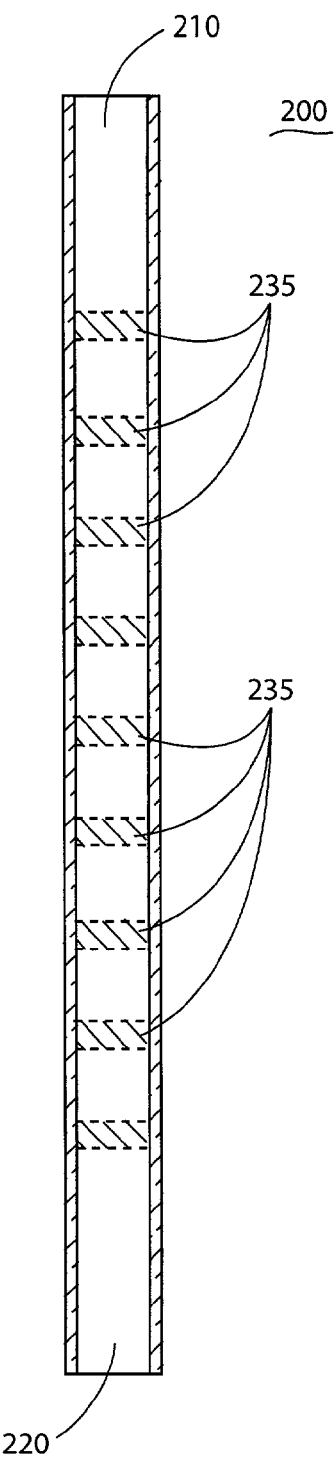

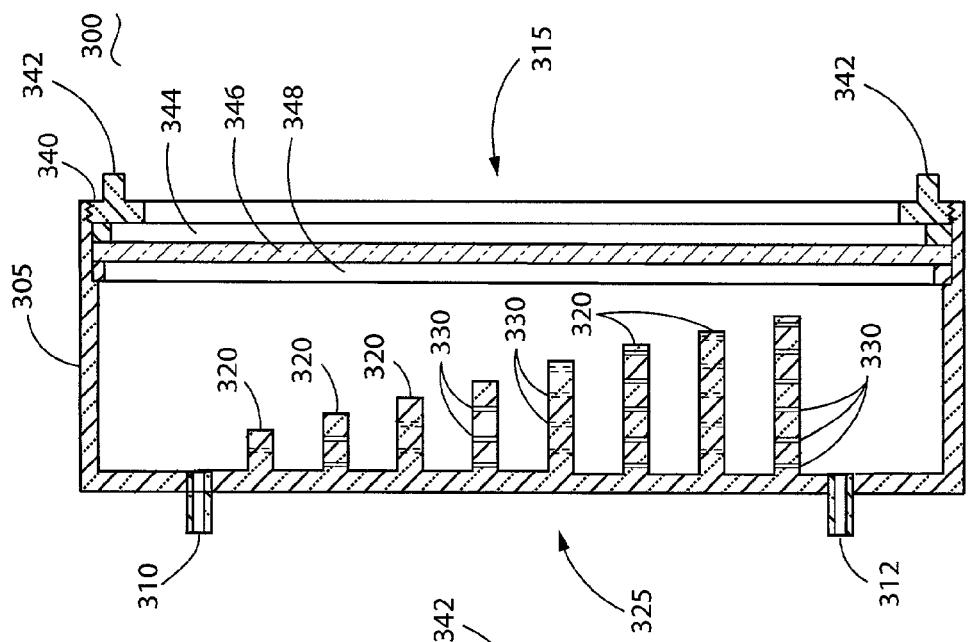
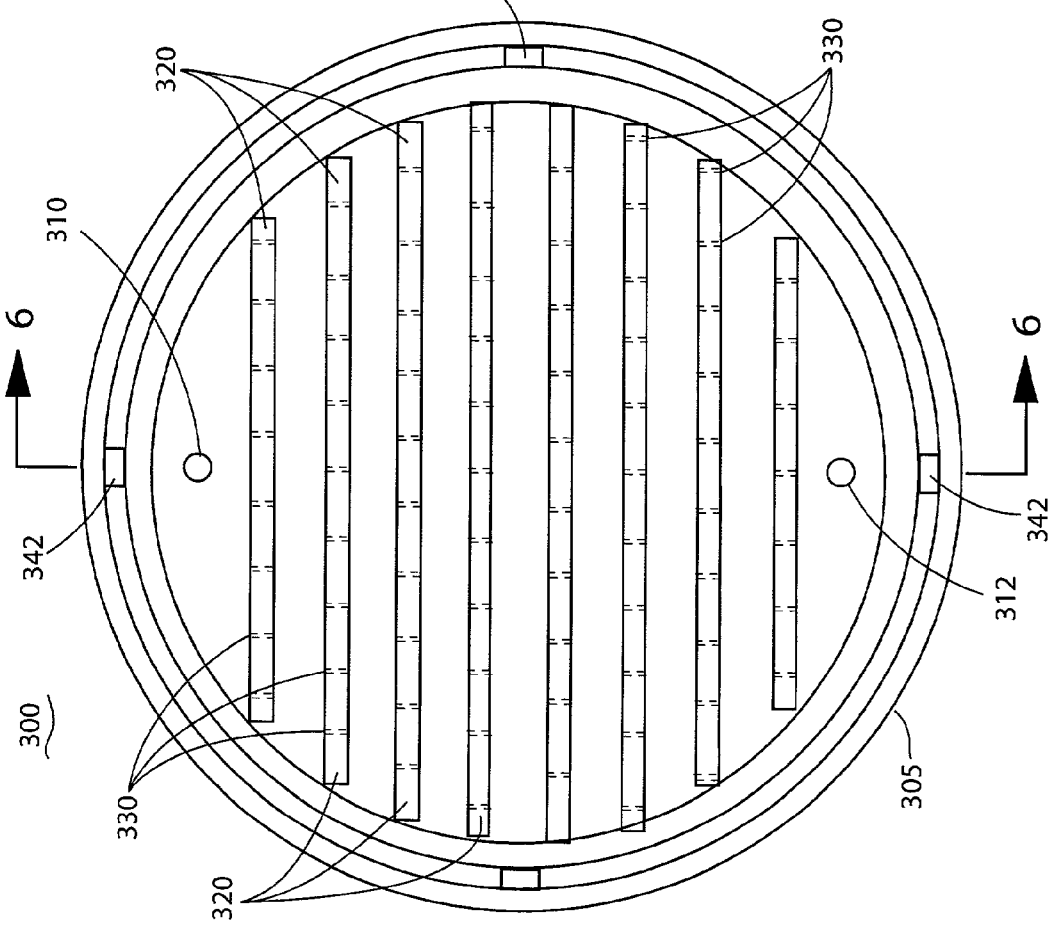

BLOOD IRRADIATING APPARATUS

BACKGROUND OF THE INVENTION

1. Field of the Invention

The present invention relates generally to disinfecting blood, and more particularly to an apparatus configured to irradiate blood by controlled exposure to an ultraviolet light source.

2. Description of the Prior Art

Subjecting blood to ultraviolet light irradiation has been known to kill and eliminate a host of bacterial infections, germs, viruses, and other harmful pathogens and toxins from the body. In undergoing ultraviolet light irradiation treatment, the blood is typically removed from a patient's circulatory system and exposed to an ultraviolet light source before being reintroduced into the patient's body.

A number of devices have been developed, in the past, in an attempt to properly expose germs, bacteria, and other pathogens present in blood plasma to ultraviolet light irradiation. Existing irradiation systems, however, have not been successful in providing a broad level of flexibility in the duration of treatment or the range and intensity of ultraviolet light irradiation provided. As a result, existing treatments using irradiation therapy have generally been limited in scope to a narrow spectrum of ultraviolet light and have been quite restrictive in the combinations of irradiation duration and intensity provided. The limited flexibility provided by existing systems regarding the time and intensity of treatment often results in blood plasma that is untreated or under treated for various ailments. Additionally, existing blood irradiation systems provide very limited, if any, flexibility in the amount of turbulence provided to the blood during treatment and do not provide a practical and efficient way to strategically vary the wide range of other treatment parameters including, for example, the flow velocity or flow path that the blood will be exposed to during treatment.

Accordingly, there is an established need for a practical blood irradiating apparatus solving the aforementioned problems and providing for strategically controlled treatment of blood capable of providing variable light intensity and duration during treatment as well as flexible and controlled blood flow turbulence.

SUMMARY OF THE INVENTION

The present invention is directed to a blood irradiating apparatus configured to irradiate blood by controlled and strategic exposure to ultraviolet light of varying wavelength and intensity.

An object of the present invention is to provide a blood irradiating apparatus that is capable of destroying germs, viruses, bacteria and eliminating a variety of toxins in the blood.

A further object of the present invention is to provide a blood irradiating apparatus capable of focusing ultraviolet light strategically within a narrow spectrum, as desired, to treat and irradiate specific varieties of germs, bacteria, or viruses in the blood.

Yet another object of the present invention is to provide a blood irradiating apparatus that is capable o irradiating a wide variety of different pathogens and combinations of toxins in the blood.

A further object of the present invention is to provide a blood irradiating apparatus that is capable of irradiating blood using a varying spectrum of ultraviolet light.

Another object of the present invention is to provide a blood irradiating apparatus that wherein the time and intensity of blood irradiation is variable.

An additional object of the present invention is to provide a blood irradiating apparatus that is capable of permitting laminar blood flow through a variety of cuvettes.

Another object of the present invention is to provide a blood irradiating apparatus capable of irradiating blood through a number of cuvettes having varying configurations.

An additional object of the present invention is to provide a blood irradiating apparatus wherein the blood can be strategically exposed to varying levels of turbulence during treatment.

In accordance with a first aspect of the invention, a blood irradiating apparatus is provided including a plurality of irradiating chambers having a base and an openable cover. Each irradiating chamber will include a number of ultraviolet light bulbs configured to provide a wide spectrum of ultraviolet light of differing wavelengths. A number of cuvettes permeable to ultraviolet light will be disposed in the irradiating chamber and configured to permit blood to flow in a turbulent manner sufficient to maximize exposure to ultraviolet light.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which:

FIG. 3 is a top view of the laminar-flow cuvette for use in the blood irradiating apparatus shown in accordance with an exemplary embodiment of the present invention;

FIG. 4 is a cross-sectional view of the laminar-flow cuvette of FIG. 3 taken along line 4—4;

FIG. 5 is a top view of a cascade-flow cuvette for use in the blood irradiating apparatus shown in accordance with an exemplary embodiment of the present invention;

FIG. 6 is a cross-sectional view of the cascade-flow cuvette of FIG. 5 taken along line 6—6;

DETAILED DESCRIPTION OF THE PREFERRED EMBODIMENTS

Shown throughout the figures, the present invention is generally directed towards a blood irradiating apparatus configured to disinfect blood by controlled treatment with ultraviolet light. The blood irradiating apparatus of the present invention provides the capability of strategically focusing the intensity of ultraviolet light within a narrow spectrum to irradiate specific bacteria or viruses as desired. Along with controlling the wavelength of ultraviolet light utilized during irradiation, the blood irradiating apparatus of the present invention provides the ability to strategically control the blood flow turbulence and duration of exposure to provide substantially enhanced blood treatment capabilities.

Figure 1:
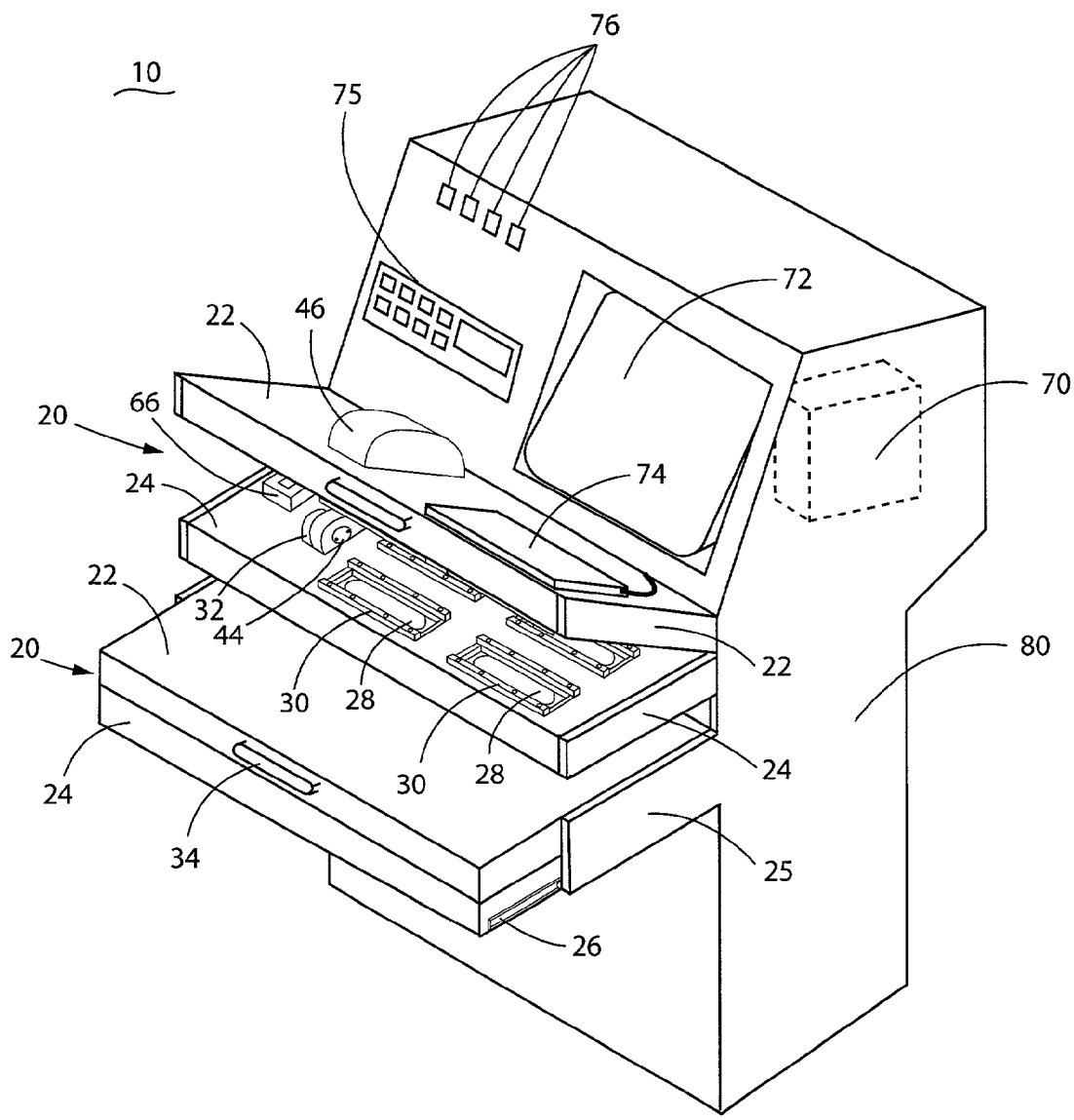
FIG. 1 is a perspective view of the blood irradiating apparatus shown without the cuvettes in place and with the irradiating chamber in an open configuration.
Figure 2:
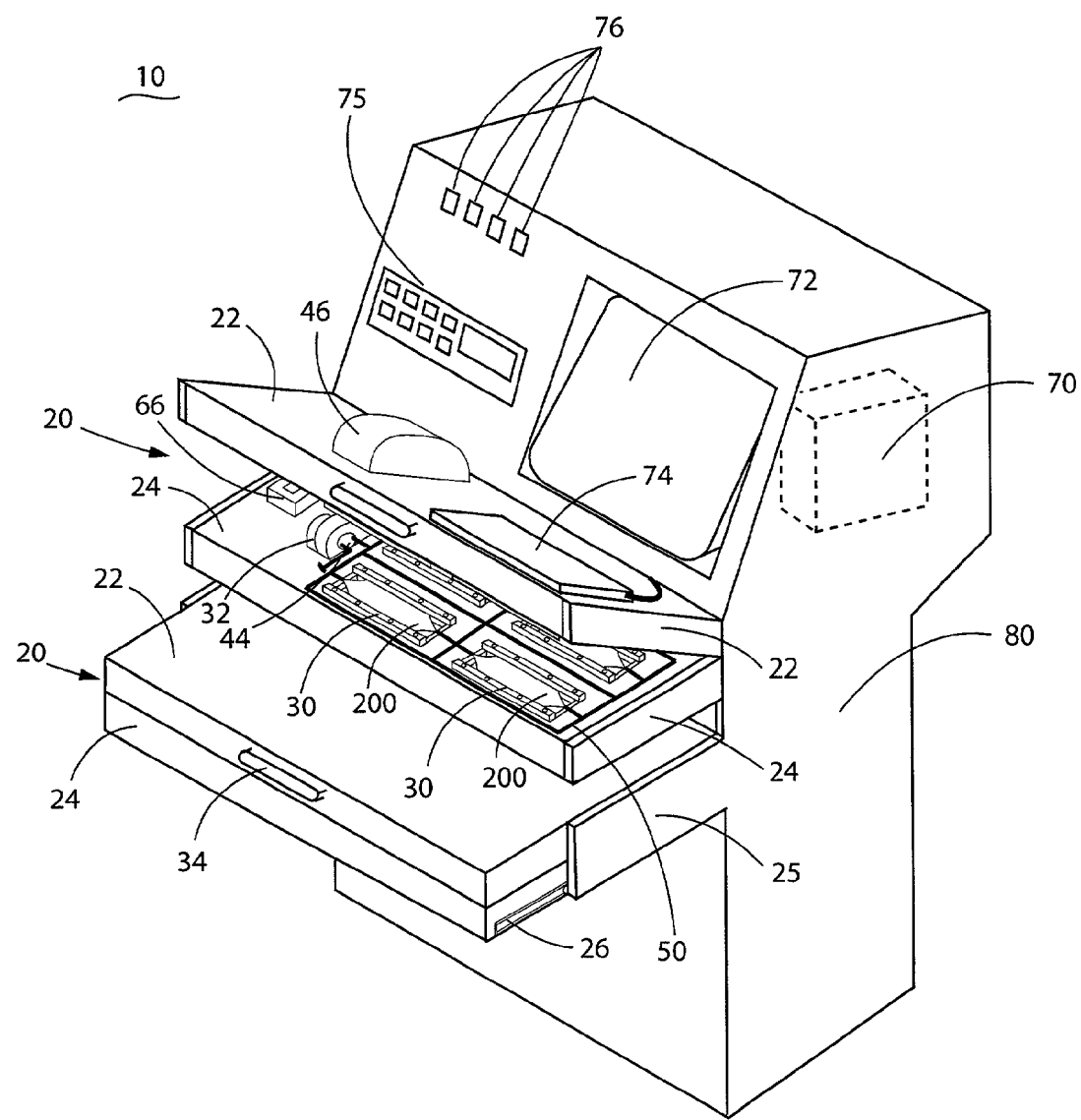
FIG. 2 is a perspective view of the blood irradiating apparatus shown with the cuvettes positioned and connected and with the irradiating chamber in an open configuration.

An illustrative embodiment of the blood irradiating apparatus 10 of the present invention is shown in FIGS. 1 and 2. Although the blood irradiating apparatus 10 of the present invention may be structured in a wide variety of configurations, in the preferred embodiment it will be a free-standing central unit 80 as shown. The blood irradiating apparatus 10 of the present invention will preferably have a number of irradiating chambers 20 disposed within the central unit 80 and configured to receive blood. Each irradiating chamber 20 will preferably include a cover 22 and a base 24 as best illustrated in FIGS. 1 and 2. The cover 22 and base 24 may be configured, if desired, in a generally hinged relationship to permit easy access to the interior of the irradiating chamber 20 as shown. Additionally, it will be appreciated that the irradiating chambers 20 may be configured to slide outwards to provide easy and convenient access as shown in FIGS. 1 and 2. A wide variety of known means may be utilized to facilitate such outward movement of the irradiating chamber 20. In the preferred embodiment, a conventional drawer mount 25 and cooperating mounting hardware 26 will be utilized as shown.

Figure 7:
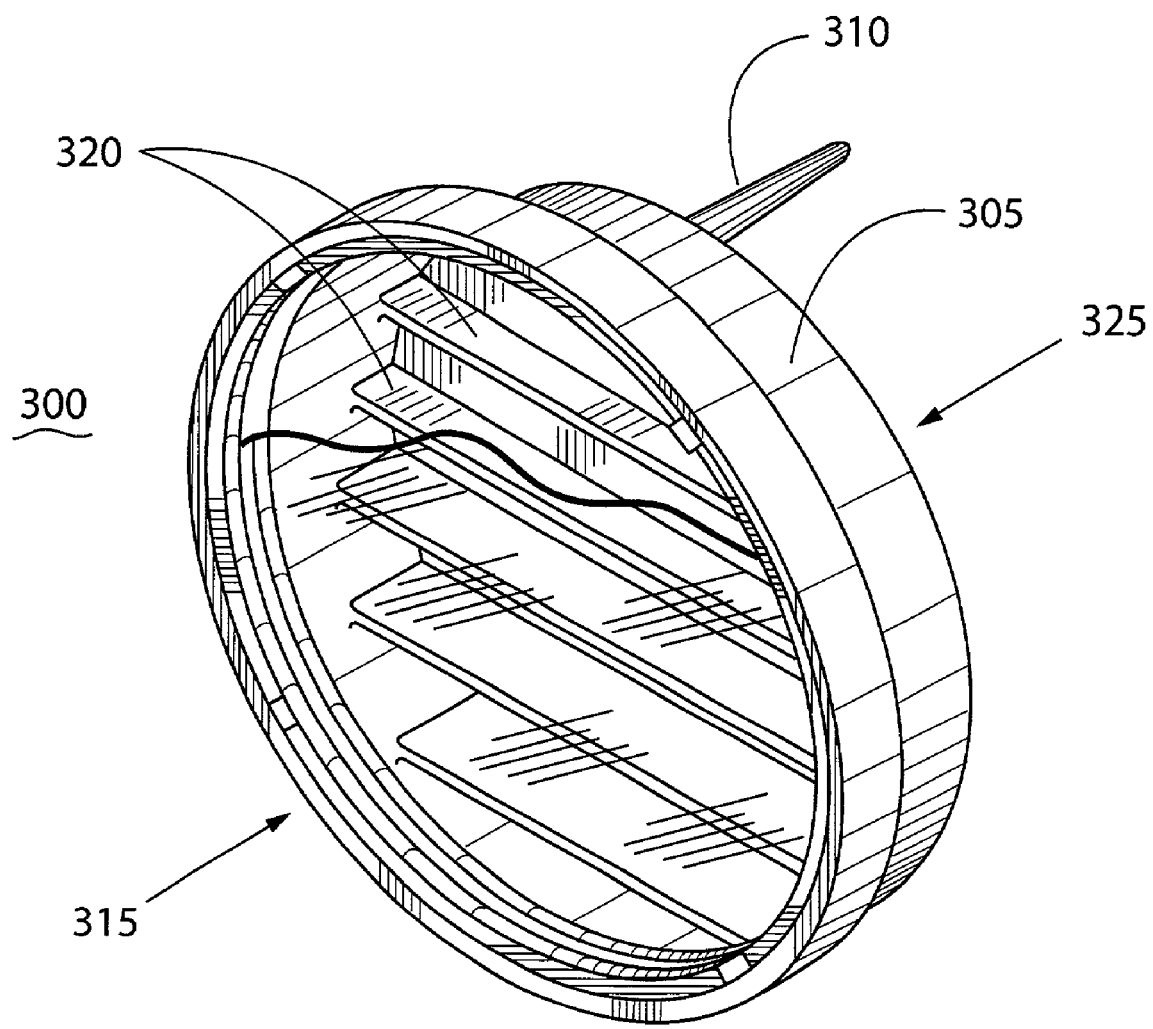
FIG. 7 is a perspective close-up view of the cascade-flow cuvette of the present invention.
Figure 8:
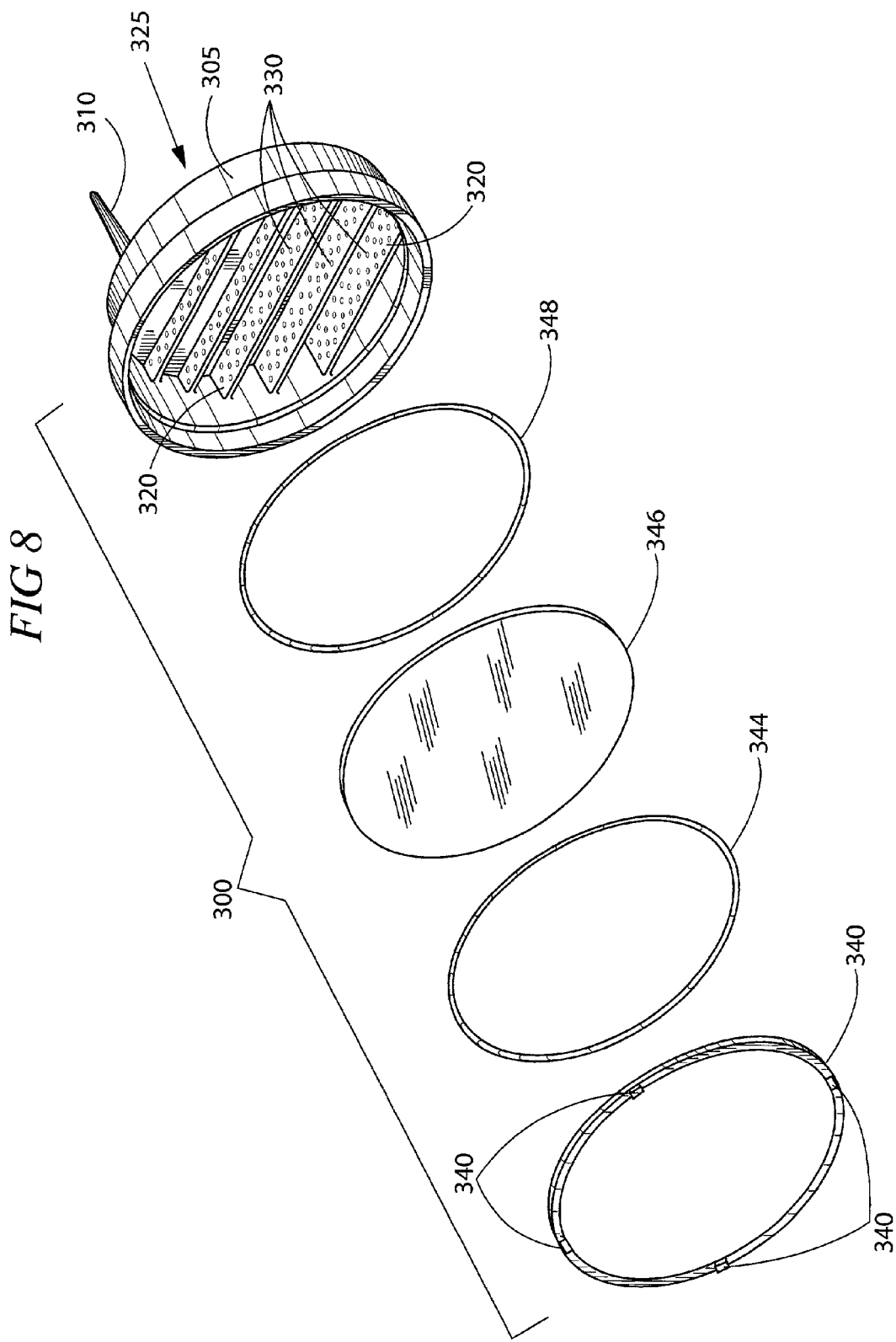
FIG. 8 is a perspective exploded view of the cascade-flow cuvette of the present invention along with various components before assembly.
Figure 9:
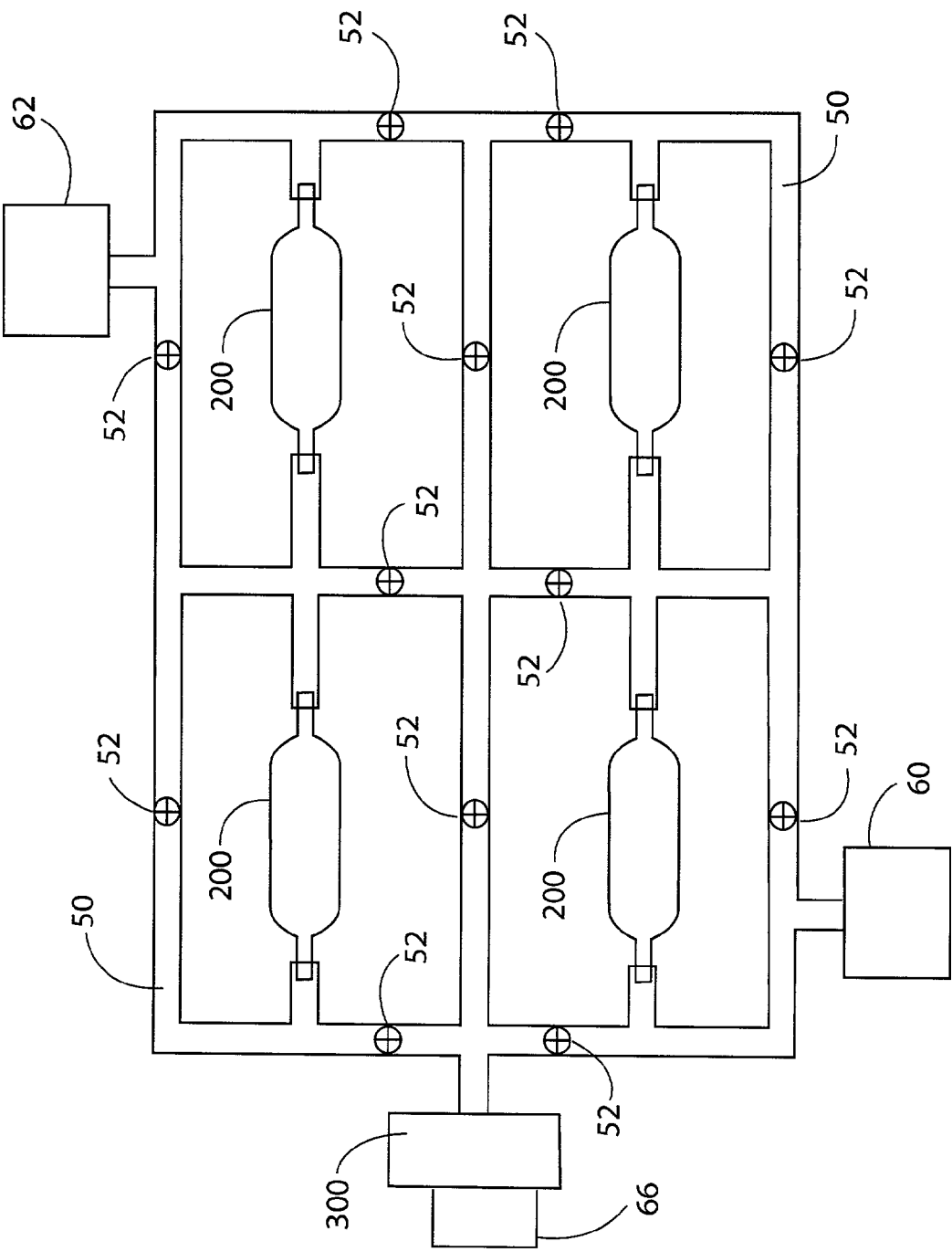
FIG. 9 is a schematic view showing the blood irradiating apparatus in accordance with an exemplary embodiment of the present invention.

The blood irradiating apparatus 10 of the present invention is configured for use with a number of laminar-flow and cascade-flow cuvettes 200, 300 as best shown in FIGS. 3–8. These cuvettes 200,300 are configured to be assembled in place with a tubing structure 50 as shown in FIGS. 2 and 9 and are structured to maximize exposure of blood to ultraviolet light. Both the cascade-flow cuvette 200 and the laminar-flow cuvette 300 will be described in more detail herein.

The blood irradiating apparatus 10 of the present invention is shown in FIG. 1 without the cuvettes 200, 300 in place in order to clearly depict details of the irradiating chamber 20. As shown in FIG. 1, the cover 22 and base 24 of the irradiating chamber 20 will preferably be configured with a number of openings 28 therein to permit ultraviolet light to pass through. The base 24 of the irradiating chamber 20 may also include a number of laminar-flow cuvette holders 30 to secure the laminar-flow cuvettes during irradiation. In the preferred embodiment, at least one cascade-flow cuvette holder 32 will also be provided to secure the cascade-flow cuvette 300 during irradiation as shown in FIGS. 1 and 2.

Figure 10:
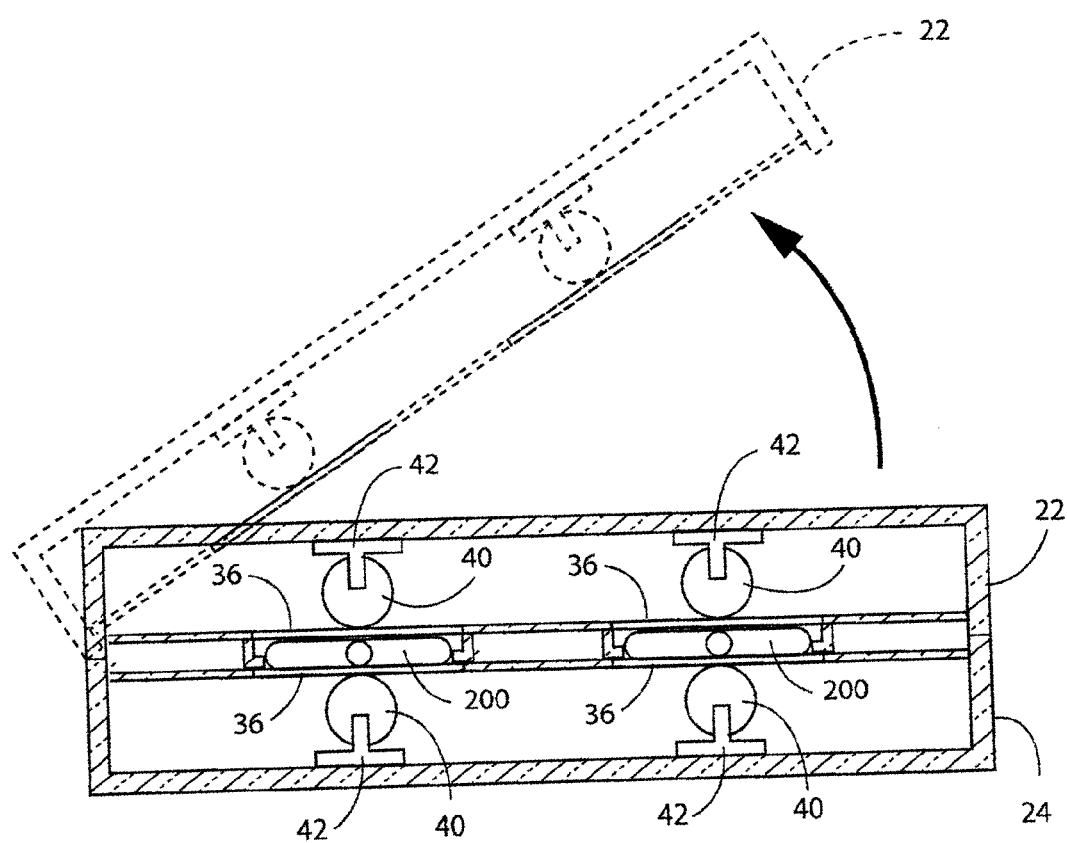
FIG. 10 is a side view showing the irradiating chamber of the present invention in accordance with an exemplary embodiment of the present invention.

A side view of the irradiating chamber 20 of the blood irradiating apparatus 10 is shown in FIG. 10. As shown, the cover 22 and the base 24 enclose a number of ultraviolet light bulbs 40 disposed therein. The ultraviolet light bulbs can be secured with a mounting bracket 42 as shown. As discussed, the cover 22 of the irradiating chamber 20 will preferably be configured in a generally hinged relationship so that it can rotate to permit easy access to the interior of the irradiating chamber 20. The cover 22 is shown with hidden lines in an open position.

Figures 11, 12:
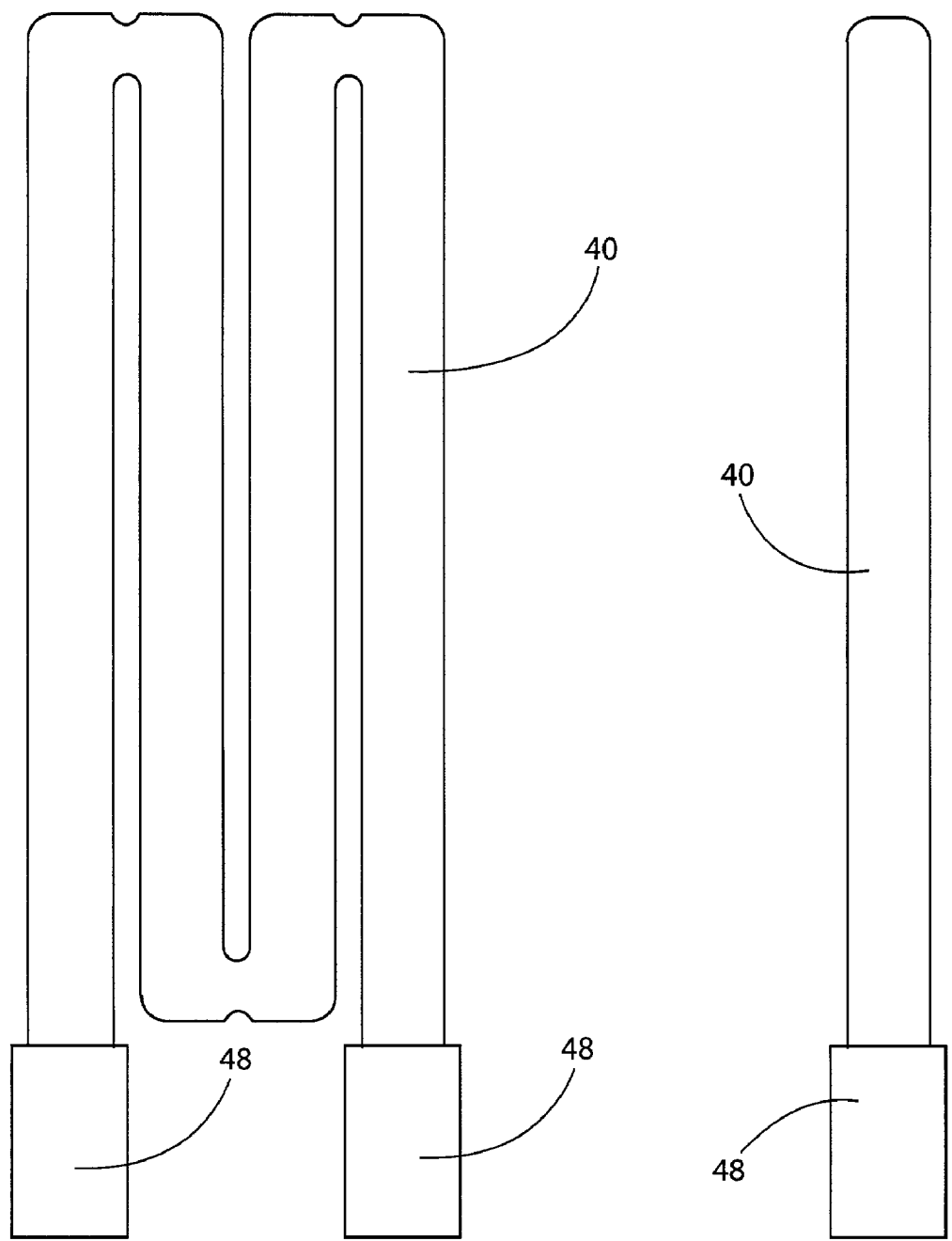
FIG. 11 is a front view showing the ultraviolet light bulb of the present invention in accordance with an exemplary embodiment of the present invention.
FIG. 12 is a side view showing the ultraviolet light bulb of the present invention in accordance with an exemplary embodiment of the present invention.

Each ultraviolet light bulb 40 will preferably be configured to provide a different intensity and wavelength of ultraviolet light for irradiating a variety of viral and bacterial diseases. As such, it will be possible to treat blood with a wide spectrum of ultraviolet light, as desired, to more thoroughly irradiate and treat blood for different purposes depending upon the specific health condition of a patient. The ultraviolet light bulb 40 of the present invention may be structured in any of a wide variety of configurations without departing from the present invention. In a most preferred embodiment, the ultraviolet light bulb 40 will be structured in a space-saving flat configuration as illustrated in the side view of FIG. 12. FIG. 11 shows a front view of an exemplary embodiment of the ultraviolet light bulb 40 of the present invention. In a most preferred embodiment, the ultraviolet light bulb 40 of the present invention will be configured with conventional terminals 48 to facilitate convenient replacement of the ultraviolet light bulbs as needed.

As previously discussed, the cover 22 and base 24 of the irradiating chamber 20 will preferably be configured with a number of openings 28 disposed therein to permit the ultraviolet light to pass to the cuvettes 200, 300. If desired, the opening 28 may be provided with a translucent covering. In a most preferred embodiment, a glass plate 36 may be positioned over the opening 28 and secured in place as shown in FIG. 10. As shown in FIG. 1, a vertically disposed ultraviolet light bulb 44 will also be utilized in the preferred embodiment as shown. The vertically disposed ultraviolet light bulb 44 will be configured to irradiate blood flowing through the cascade-flow cuvette 300 as will be described in more detail herein. In order to accommodate the cascade-flow cuvette 300 and the vertically disposed ultraviolet light bulb 44, the cover 22 of the irradiating chamber 20 may be formed with a pocket 46 therein to partially surround the ultraviolet light bulb 44, cascade-flow cuvette 300, and cascade-flow cuvette holder 32 as best shown in FIG. 1.

The blood irradiating apparatus 10 of the present invention will be particularly configured to permit blood to be treated utilizing any of a wide variety of ultraviolet light sources of differing intensity and wavelength. As best shown in the schematic view of FIG. 9, the blood irradiating apparatus 10 of the present invention is preferably configured with conduit means configured to direct blood through specific cuvettes 200, 300 as desired. In the preferred embodiment, the conduit means will comprise an adaptable tubing structure 50 as shown in FIG. 9. The adaptable tubing structure 50 will be configured to transport blood through specific cuvettes 200, 300 and permit a user to carefully control the intensity and wavelength that the blood will be exposed to. It will be appreciated that the tubing structure 50 shown is exemplary in nature and any of a wide variety of other conduit means may be utilized without departing from the present invention. If desired, a variety of valves 52 may be included in the tubing structure to facilitate strategic flow of the blood throughout the irradiating chamber 20 of the blood irradiating apparatus 10 of the present invention. As shown in FIG. 9, the blood irradiating apparatus will also preferably include an untreated blood holding tank 60 and a treated blood holding tank 62 as best shown in FIG. 9. The untreated blood will preferably flow through the irradiating chamber 20 for treatment via tubing structure 50 and cuvettes 200, 300 and exit to the treated blood storage tank 62 for storage after ultraviolet light exposure. In order to facilitate blood movement throughout the blood irradiating apparatus 10 of the present invention, a conventional pump 66 may be provided as shown in FIGS. 1 and 2.

The blood irradiating apparatus 10 of the present invention, as shown in FIGS. 1 and 2, may include a conventional processor 70 having a keyboard 72 and a monitor 74 as shown. The processor 70 may be used to monitor any of a variety of different parameters during blood irradiation. For example, the processor 70 may be configured to monitor the velocity of blood flow, temperature of the blood during irradiation, ultraviolet bulb intensity, blood irradiation time, and a host of other variables, as desired, during irradiation. Additionally, the blood irradiating apparatus 10 of the present invention may include, if desired, a manual operation panel 75 for instances in which use of the monitor 72 and keyboard 74 are not required. A number of switches 76 may also be provided, if desired, to automate different processes of the blood irradiating apparatus 10 of the present invention. These switches may control, for example, the activation or intensity of individual lamps and the flow velocity of the blood through the cuvettes 200, 300.

The laminar-flow cuvette 200 will preferably comprise a generally flat main body 230 having a tapered first end 210 and a tapered second end 220 and enclosing a flow passageway therein as illustrated in FIGS. 3–4. Preferably, a number of pins 235 will be disposed within the laminar-flow cuvette 200 in order to cause a sufficiently turbulent flow of blood through the main body 230 of the laminar-flow cuvette 200. In the preferred embodiment, the pins 235 will be configured to provide a slightly turbulent flow sufficient to optimize exposure of the blood flowing through the laminar-flow cuvette 200 to ultraviolet irradiation. In a most preferred embodiment, the pins 235 will be arranged in a generally staggered configuration as shown in FIG. 3. The laminar-flow cuvette 200 of the present invention will preferably be formed of a substantially strong and translucent material such as, for example, glass or high-density plastic.

In addition to the laminar-flow cuvettes shown, the blood irradiating apparatus 10 of the present invention will include at least one cascade-flow cuvette 300. An exemplary embodiment of the cascade-flow cuvette 300 of the present invention is illustrated in FIGS. 5–8. A front view of the cascade-flow cuvette 300 is illustrated in FIG. 5.

The cascade-flow cuvette 300 of the present invention includes a generally cylindrical housing 305 enclosing a flow passageway therein and having a front side 315 and a rear side 325 as shown. The cascade-flow cuvette 300 preferably includes an inlet 310 disposed near the top end of the housing 305 and an outlet 312 disposed near the bottom end of the housing 305 as shown. A number of steps 320 are preferably disposed within the cascade-flow cuvette 300 in order to cause a sufficiently turbulent flow of blood. In the preferred embodiment, the smallest sized step 320 will be located near the top end of the housing 305 of the cuvette 300 with the size of the steps 320 gradually increasing towards the bottom end of the cuvette 300 as best illustrated in the cross-sectional view of FIG. 6 taken along line 6—6 of FIG. 5.

The stepped configuration of the cascade-flow cuvette 300 of the present invention assists in optimizing exposure of the blood to ultraviolet irradiation during treatment. As shown in the figures, the steps 320 of the cascade-flow cuvette 300 of the present invention will be configured with a number of apertures 330 disposed therein. The apertures 330 in the steps 320 of the cascade-flow cuvette 300 will permit a quantity of blood to flow from a higher step 320 to a lower step 320 of the cascade-flow cuvette 300 providing a sufficient degree of turbulence to optimize exposure of the blood to ultraviolet irradiation as previously discussed.

The cascade-flow cuvette 300 of the present invention is shown in perspective view in FIG. 7. An exploded perspective view is depicted in FIG. 8 and shows several components of the cascade-flow cuvette 300 before assembly. It will be appreciated, of course, by those skilled in the art that a variety of different structural configurations may be utilized for the cascade-flow cuvette 300 without departing from the present invention. Along these lines, as shown in FIG. 8, the front side 315 of the cascade-flow cuvette 300 of the present invention may be comprised of a variety of different components. In a most preferred embodiment, the front 315 of the cascade-flow cuvette 300 preferably includes a first sealing ring 348, a transparent cover 346, a second sealing ring 344, and a threaded outer ring 344. The threaded outer ring 344 may be configured, if desired, with a number of tabs 342 disposed thereon to facilitate easier installation and removal of the cover 346 on the cascade-flow cuvette. Removal of the cover 346 may be desired, for example, in order to clean or disinfect the cascade-flow cuvette 300. Of course, if desired, the cascade-flow cuvette 300 may also be configured to be disposable after a single use so as to substantially reduce the risk of contamination of blood between irradiation treatments.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

I claim:

1. A blood irradiating apparatus for treating blood with ultraviolet light comprising:
    a plurality of irradiating chambers, each of said plurality of irradiating chambers including a base and an openable cover to provide access therein,
    a plurality of ultraviolet light bulbs disposed within each of said irradiating chambers, said ultraviolet light bulbs configured to provide a wide spectrum of ultraviolet light of differing wavelengths,
    at least one laminar-flow cuvette and at least one cascade-flow cuvette disposed within said irradiating chambers and permeable to ultraviolet light from said ultraviolet light bulbs, said laminar-flow cuvette and said cascade-flow cuvette configured to permit blood to flow therethrough in a turbulent manner sufficient to maximize exposure of said blood to said ultraviolet light, and
    an adaptable tubing structure configured to strategically transport said blood through said laminar-flow cuvette and said cascade-flow cuvette for exposure to said ultraviolet light during treatment.

2. A blood irradiating apparatus for treating blood with ultraviolet light as recited in claim 1, wherein said laminar-flow cuvette provides a turbulent flow passageway for blood during treatment and comprises:
    a generally flat main body having a tapered first end and a tapered second end and enclosing a flow passageway therein,
    said generally flat main body having a plurality of pins disposed therein to provide for turbulent blood flow during treatment.

3. A blood irradiating apparatus for treating blood with ultraviolet light as recited in claim 2, wherein said cascade-flow cuvette provides a turbulent flow passageway for blood during treatment and comprises:

a generally cylindrical housing having a front side and a rear side and defining a turbulent flow passageway therebetween, an inlet disposed near a top end of said cascade-flow cuvette and an outlet disposed near a bottom end of said cascade-flow cuvette, said inlet and said outlet configured to permit ingress and egress of blood flow into said cascade-flow cuvette during treatment, and a plurality of steps disposed within said cuvette between said inlet and said outlet.

4. A blood irradiating apparatus for treating blood with ultraviolet light as recited in claim 3, wherein each of said plurality of steps includes a plurality of apertures disposed therein to permit said blood to flow therethrough.

5. A blood irradiating apparatus for treating blood with ultraviolet light comprising:

a plurality of irradiating chambers, each of said plurality of irradiating chambers including a base and an openable cover to provide access therein;

a plurality of ultraviolet light bulbs disposed within each of said irradiating chambers, said ultraviolet light bulbs configured to provide a wide spectrum of ultraviolet light of differing wavelengths;

a plurality of cuvettes disposed within said irradiating chambers and permeable to ultraviolet light from said ultraviolet light bulbs, said plurality of cuvettes configured to permit blood to flow therethrough in a turbulent manner sufficient to maximize exposure of said blood to said ultraviolet light, said plurality of cuvettes including at least one laminar-flow cuvette and at least one cascade-flow cuvette; and an adaptable tubing structure configured to strategically transport said blood through said plurality of cuvettes for exposure to said ultraviolet light during treatment.

6. A blood irradiating apparatus for treating blood with ultraviolet light as recited in claim 5, wherein said laminar-flow cuvette provides a turbulent flow passageway for blood during treatment and comprises:

a generally flat main body having a tapered first end and a tapered second end and enclosing a flow passageway therein, said generally flat main body having a plurality of pins disposed therein to provide for turbulent blood flow during treatment.

7. A blood irradiating apparatus for treating blood with ultraviolet light as recited in claim 6, wherein said cascade-flow cuvette provides a turbulent flow passageway for blood during treatment and comprises:

a generally cylindrical housing having a front side and a rear side and defining a turbulent flow passageway therebetween, an inlet disposed near a top end of said cascade-flow cuvette and an outlet disposed near a bottom end of said cascade-flow cuvette, said inlet and said outlet configured to permit ingress and egress of blood flow into said cascade-flow cuvette during treatment, and a plurality of steps disposed within said cuvette between said inlet and said outlet.

8. A blood irradiating apparatus for treating blood with ultraviolet light as recited in claim 7, wherein each of said plurality of steps includes a plurality of apertures disposed therein to permit blood flow therethrough.

9. A blood irradiating apparatus for treating blood with ultraviolet light as recited in claim 8, wherein each of said plurality of steps gradually increases in width towards said bottom end of said cascade-flow cuvette.

10. A blood irradiating apparatus for treating blood with ultraviolet light as recited in claim 9, further comprising a processor configured to control and monitor blood irradiating operations.

11. A blood irradiating apparatus for treating blood with ultraviolet light as recited in claim 5, wherein said laminar-flow cuvette is disposable.

12. A blood irradiating apparatus for treating blood with ultraviolet light as recited in claim 5, wherein said cascade-flow cuvette is disposable.

13. A blood irradiating apparatus for treating blood with ultraviolet light comprising:

a plurality of irradiating chambers housed in a central unit, at least one of said irradiating chambers configured to slide outwards from said central unit to provide convenient access thereto, each of said plurality of irradiating chambers including a base and an openable cover disposed in a generally hinged relationship to said base to provide access therein, a plurality of ultraviolet light bulbs disposed within each of said irradiating chambers, said ultraviolet light bulbs configured to provide a wide spectrum of ultraviolet light of differing wavelengths, a plurality of cuvettes disposed within said irradiating chambers and permeable to ultraviolet light from said ultraviolet light bulbs, said plurality of cuvettes configured to permit blood to flow therethrough in a turbulent manner sufficient to maximize exposure of said blood to said ultraviolet light, at least one of said plurality of cuvettes comprising a cascade-flow cuvette; and conduit means configured to strategically transport said blood through said plurality of cuvettes for exposure to said ultraviolet light during treatment.

14. A blood irradiating apparatus for treating blood with ultraviolet light as recited in claim 13, wherein said cascade-flow cuvette can be disassembled for cleaning.

* * * * *